United States Patent [19]

Kossoff

[11] 4,094,306
[45] June 13, 1978

[54] APPARATUS FOR ULTRASONIC EXAMINATION

[75] Inventor: George Kossoff, Northbridge, Australia

[73] Assignee: The Commonwealth of Australia, c/o The Department of Health, Phillip, Australia

[21] Appl. No.: 681,037

[22] Filed: Apr. 28, 1976

[30] Foreign Application Priority Data

May 1, 1975 Australia ............... PC1443

[51] Int. Cl.$^2$ ............................................. A61B 10/00
[52] U.S. Cl. ...................... 128/2 V; 73/620; 128/2.05 Z; 128/24 A
[58] Field of Search ............... 128/2 V, 2.05 Z, 24 A; 73/67.8 S

[56] References Cited

U.S. PATENT DOCUMENTS

| 3,470,868 | 10/1969 | Krause et al. | 128/2 V |
| 3,480,002 | 11/1969 | Flaherty et al. | 128/2 V |
| 3,547,101 | 12/1970 | Rosauer | 128/2 V |
| 3,577,772 | 5/1971 | Perilhou et al. | 128/2 V X |
| 3,603,303 | 9/1971 | Stouffer | 128/2 V |
| 3,752,255 | 8/1973 | Hill et al. | 73/67.8 S X |
| 3,765,403 | 10/1973 | Brenden | 128/2 V |
| 3,936,791 | 2/1976 | Kossoff | 128/2 V X |
| 3,973,235 | 8/1976 | van der Burgt | 128/2 V X |
| 3,990,296 | 11/1976 | Erikson | 128/2 V X |

Primary Examiner—Kyle L. Howell

[57] ABSTRACT

Apparatus for the pulse-echo ultrasonic examination of an object comprised of transducer means for transmitting pulses of ultrasonic energy and receiving reflected echoes of said pulses immersed in a coupling medium contained within a housing, the pulses being transmitted and echoes received through an aperture in the housing which may be covered with a flexible coupling membrane and the housing including a storage header tank open to the atmosphere to maintain the pressure to the coupling medium on the membrane constant during flexing of the membrane.

5 Claims, 10 Drawing Figures

TRANSMITTER & RECEIVER SWITCHING

APPARATUS FOR ULTRASONIC EXAMINATION

This invention relates to the technique of ultrasonic echoscopy of objects and in particular to means for decreasing the time required for examination of an object using the pulse-echo ultrasonic technique and for improving the clarity and hence the utility of the examination results. It is particularly, but not solely, directed to the use of this technique in medical diagnostic examination.

Ultrasonic echoscopy provides information about an examined object which may be displayed in the form of an ultrasonic echogram. Such an echogram consists of a display of acoustic impedance discontinuities or reflecting surfaces in the object. It is obtained by directing a short pulse of ultrasonic energy, typically in the 1–30 MHz frequency range, into the examined object where any acoustic impedance discontinuities in the object reflect and return some of the energy in the form of an echo. This echo is received, converted into an electric signal and displayed as an echogram on a cathode ray oscilloscope, a film, a chart or the like.

The echogram may constitute either a one dimensional or a two dimensional representation and in both cases the information is contained in the position and magnitude of the echo displayed. In a one dimensional display, the position along a base line is used to indicate the distance to the reflecting surface whilst the magnitude of the echo is displayed for example as a deflection of the base line "A mode" or as an intensity change "B mode". In a two dimensional display, the position along a base line is used to indicate the distance to the reflecting surface as in a one dimensional display, and the direction of the base line is used to represent the direction of propagation of the acoustic energy. The two dimensional display is obtained by changing this direction of propagation of the acoustic energy and by instituting a similar but not necessarily identical movement of the base line of the display. The magnitude of the echo is displayed as for a one dimensional display, for example, as a deflection of the base line or as an intensity change.

The technique of ultrasonic echoscopy is used in medical diagnosis to obtain information about the anatomy of patients. The application of this technique is now widely investigated and is described, for example, by D.E. Robinson in Proceedings of the Institution of Radio and Electronics Engineers Australia, Vol. 31, No. 11, pages 385 – 392, November, 1970: "The Application of Ultrasound in Medical Diagnosis". As pointed out in this article, ultrasonic echoscopy may be used to produce displays resembling anatomical cross-sections which have proved clinically useful when the desired information concerns physical dimensions, shapes of organs or structures or the like. Ultrasonic echography has proved of particular value as a diagnostic aid in the abdomen and pregnant uterus, eye, breast, brain, lung, kidney, liver and heart, these being areas of soft tissue with little bone and air. In general, the technique is considered to complement other techniques to provide a more complete picture of the patient's condition, however, particularly in pregnancies, ultrasonic echoscopy may be useful in place of X-rays where the latter may not give sufficient information or may be dangerous. In medical use, a pulse of ultrasonic energy is transmitted into a patient in a known direction and echoes are received from reflecting surfaces within the body. The time delay between a transmitted pulse and the received echo depends on the distance from the transmitter to the reflecting surface and the distance information so obtained may be displayed in a suitable way for interpretation and clinical use as a one dimensional range reading or as a two dimensional cross section as previously described.

In one presently known form of ultrasonic diagnostic examination, a single transducer is used and it is physically moved to various positions around the patient. At each of these positions the beam is swept with an oscillatory motion while constrained to remain within a single plane by mechanical oscillation of the transducer, to obtain the required scan pattern. By the use of suitable deflection circuits, for example, in a cathode ray display tube, a line is caused to follow the motions of the beam axis and echoes within the part examined are thus displayed in their correct geometrical positions. By way of example, for transverse sections, the transducer may be moved horizontally in a 150° arc around a patient who is substantially erect while undergoing ± 15° oscillations and for longitudinal sections the transducer may be moved vertically while undergoing ± 30° oscillations.

It has, however, been found that in such systems where the transducer is physical moved around the patient this movement leads to a limitation on the examination time of between ten and twenty seconds for each cross-sectional visualization due to mechanical inertia and, in the case where the transducer is coupled to the patient via a coupling medium such as water, the generation of turbulance by the transducer when it moves quickly in the coupling medium.

Several alternative forms of ultrasonic examination equipment have been devised which will avoid the limitations discussed above and thus enable a speeding up of the time required for each cross-sectional visualization. It will be apparent that a reduction in examination time of a patient will lead to a technical improvement in the resultant echograms as the effects of movement of the part under examination will be reduced. In addition, a reduction in examination time of a patient will have the economic advantage that more cross-sectional visualization and hence more examinations will be able to be performed in a given time.

In the currently used two dimensional B mode systems of ultrasonic examination, a single transducer is either mechanically driven or manually operated to obtain an echogram. To enable examination of a region of interest, for example of a patient, the plane of scan is adjusted as required, an echogram obtained in that plane, and then the plane of scan moved, and so on, usually in such a way as to examine parallel sections of the region of interest. As each cross-section visualization using the known systems requires from ten to twenty seconds, the entire examination may take up to half an hour or so. Such a long examination time is undesirable for a number of reasons. Firstly, there can be considerable movement during the examination period, particularly of the fetus in a pregnant uterus, blurring individual echograms and causing difficulty in interpreting a full set of cross-sectional visualization over a region of interest. Furthermore, a prolonged examination is often not possible or is at least most undesirable when the technique is used in the examination of sick patients. Of course, a lengthy examination time precludes the use of the technique as a screening test, and the reduced throughput of patients has an obviously deleterious effect on the economics of the technique.

It is therefore an object of the present invention to provide apparatus for ultrasonic examination of an object by the pulse-echo technique which is capable of performing a complete ultrasonic examination in a time considerably less than that possible at present. As will be appreciated from the above, any reduction of the time necessary for the examination will have the further benefit that the quality of the echograms which are obtained will be improved since the effects of patient movement will be reduced.

According to the present invention there is provided apparatus for the ultrasonic examination of an object comprising a housing enclosing a coupling medium, said housing being provided with an aperture therein, and transducer means contained within said housing and immersed in said coupling medium, said transducer means comprising means for transmitting pulses of ultrasonic energy through said aperture into the object and means for receiving echoes of said pulses of ultrasonic energy reflected through said aperture by acoustic impedance discontinuities within the object.

Preferably, the housing consists of a bath filled with water as coupling medium. The aperture is provided in the top of the bath which otherwise completely encloses the coupling medium. Preferably, a flexible coupling membrane such as a polythene membrane is provided to seal the aperture so as to ensure satisfactory contact between the coupling medium and the object such as a patient to be examined without loss of the coupling medium through the aperture. In one convenient arrangement particularly suitable for medical diagnostic examination, the bath is constructed in the form of a couch upon which a patient may be positioned with the body region to be examined over and in contact with the coupling membrane. Preferably also, the coupling medium is temperature controlled. Whilst the use of the flexible coupling membrane as described above is preferred as a matter of convenience, particularly where a large number of patients are to be examined, it will be apparent that use of this membrane may also be dispensed with thereby allowing direct contact of the coupling medium with the patient's skin.

As previously described, in accordance with the present invention the transducer means is immersed in the coupling medium contained within the housing. In known ultrasonic examination systems, coupling from the transducer to the patient has been achieved either by skin contact or by use of, for example, a water delay bath. Use of a water delay bath is recognised as introducing possible ambiguities due to multiple reflection, although these may be avoided by so arranging the system that the distance between the transducer and the skin surface of the patient is greater than the largest depth of penetration to be used. Nevertheless, while skin contact systems in general result in greater comfort for the patient, the resulting echograms are of less clarity, and the use of water delay bath provides better quality echograms. The present invention provides apparatus whereby these better quality echograms may be conveniently achieved.

In order to obtain good coupling between the transducer means and the flexible coupling membrane, or skin surface of the patient, in accordance with the present invention the housing is filled with the coupling medium and preferably the housing is provided with a header tank to ensure that the housing remains filled during flexing of the membrane, for example during positioning of the patient on the apparatus. Fluid pressure exerted by coupling medium stored in the header tank maintains pressure on the coupling membrane also, thereby helping to maintain close contact between the flexible membrane and the skin of the patient.

In a particularly important aspect of the present invention, the transducer means comprises a plurality of transducers mounted in a single arm, the arm being mounted within the housing by a supporting mechanism for movement thereof with respect to the object to be examined to facilitate examination thereof in any desired plane. Preferably, this supporting mechanism provides movement in the "$x$", "$y$" and "$z$" directions with respect to the object and also provides for rotation and tilting of the arm with respect to the object, thereby allowing focusing of the transducers of the arm on the desired region of the object and scanning in any desired plane. Preferably also, the arm supporting the transducers is curved thereby enabling a degree of mechanical focusing of the transducers at a point within the object to be examined. The curve of the arm may be circular, however linear arms or other non-linear arms may be used if desired.

The use of a plurality of transducers has been found to enable a speeding up of the time required for each cross-sectional visualization. In a typical operation the transducers are spatially positioned in a single plane relative to each other and to the object under examination as by mounting in an arm described above and the beam from each transducer is steered to a plurality of angular directions in this plane, for example by oscillation of the transducers in the plane of the arm. The transducers may than be energizing sequentially, the time of energizing each of the transducers being set so that the whole set of transducers is energized before the appropriate beam from each transducer has moved a significant distance. In this way an entire scanned crossection may be formed in one cycle of the transducers.

Oscillatory motion of the beam axes from the plurality of transducers in order to build up a complete cross-sectional visualization may be provided by two alternative means. The first means of obtaining oscillatory motion of the beam axes is by mechanically scanning all of the plurality of transducers either independently or simultaneously. In this case, although mechanical movement of the transducers does introduce a limitation on the scanning rate, the effect of this limitation may be minimised by providing suitable switching means which require the transducers to scan only once while obtaining a complete cross-sectional visualization. Thus, each transducer is activated in turn to direct a pulse of ultrasonic energy along the beam axis, the rate at which the transducers are activated being sufficiently fast, compared with the rate of mechanical oscillation of the transducers, that each transducer oscillates only a small distance between successive activations thereof. The final result achieved by this method of operation is that at the end of a single mechanical scan, each of the transducers has been activated whilst it's beam was directed in all required directions. It will be apparent that monitoring of the direction of the beam axes will be necessary in order to build up the complete visualization.

The alternative means of obtaining oscillatory motion of the beam axes is by use of transducer arrays at each transducer position, the arrays being appropriately designed as to be capable of being steered electronically.

In such a system there are no moving parts and the scanning rate obtainable with this system is limited only by considerations of electronic switching speeds and the rate of acquisition of ultrasonic information by the transducer after each transmitted pulse. Since such an array may be electronically steered to direct its beam in all required directions at a rate much faster than that possible when mechanical oscillation of the transducer is required, it is possible to operate this system by steering the beam from each transducer array to each of the required directions to measure the reflected echoes before activating the next transducer array and steering the beam from it to each of the required directions, and so on. It will, however, be appreciated that this plurality of transducer arrays capable of being electronically steered may also be operated in a manner similar to the operation of the mechanically oscillated transducers previously described.

In a further important aspect of the present invention, however, the individual transducers of an array which is being mechanically scanned may be energized in a "scattered" operation rather than in a sequence of energizing adjacent transducers. Thus, instead of energizing transducer No. 2 after transducer No. 1, and then transducer No. 3, transducer No. 4 and so on, in accordance with this invention transducer No. 5 in the array may be energized after transducer No. 1, then transducer No. 2 followed by transducer No. 6 and so on. It has been found that such "scattered" operation of a plurality of transducers enables even further speeding up of the visualization since it enables one transducer to be energized without having to wait for multiple reflections arising from energization of the previous transducer to die down, this being possible since the transducer is to transmit its pulse and receive reflections along a beam which is spaced substantially from the beam of the previous transducer. Since the "wait period" which can be avoided by such "scattered" operation may be of the order of 500 μ sec, a significant speeding up of the examination is thereby achieved.

In yet another mode of operation of the apparatus of the present invention the individual transducers of an array may be energized in such a manner that the time of display of echoes approximates the total available time. In the "scattered" operation described above in which the circuit conventionally includes a single deflection generator circuit for the display means, the time of display of echoes is approximately half of the total available time, the other half of the available time being taken up by time for transmission of the pulses through the coupling medium. In the present alternative mode of operation, however, it has been found that the use of two deflection generator circuits enables one pulse to be transmitted through the coupling medium during the period of display of echoes from the preceding pulse so that the display of echoes from the one pulse may commence almost immediately after conclusion of the display of echoes from the preceding pulse.

Where the plurality of transducers are mounted in a single arm in accordance with the present invention for oscillation in the plane of the arm, it is preferred that the transducers be mechanically linked for simultaneous oscillation. Thus a single motor may be utilised for oscillation of all of the transducers, and, if desired, a single monitoring device may be utilised to monitor the oscillation of all transducers since their respective beams will be fixed relative to one another. In accordance with a preferred aspect of the present invention the single arm is mounted on a supporting mechanism which provides for both rotation and tilting of the arm with respect to the object under examination. Rotation of the arm of course enables different cross-sectional visualization to be obtained without repositioning the object while tilting of the arm enables the transducers to be directed to a single point from different angles, thereby enabling inclined sections to be obtained. Appropriate drive means may be provided to perform this rotation and tilting, and monitoring means provided to measure the position of the transducers. Similarly, drive means and monitoring means are provided to move the arm in the "x", "y" and "z" directions and to monitor this movement.

Other features of the present invention are illustrated in the accompanying drawings in which.

Figure 5:
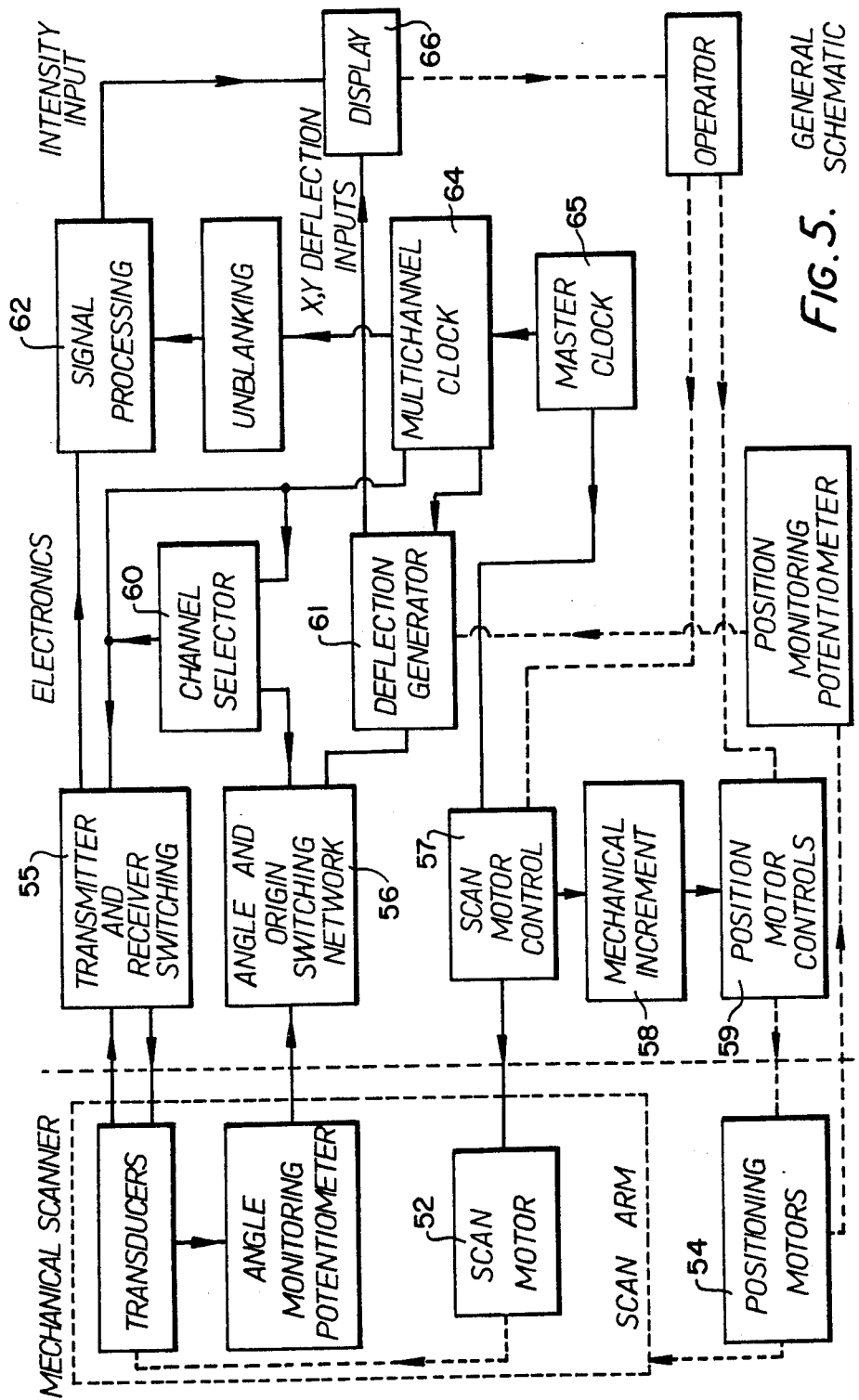
FIG. 5 shows a basic block diagram of one form of the electronics for ultrasonic examination apparatus in accordance with the present invention.
Figure 8:
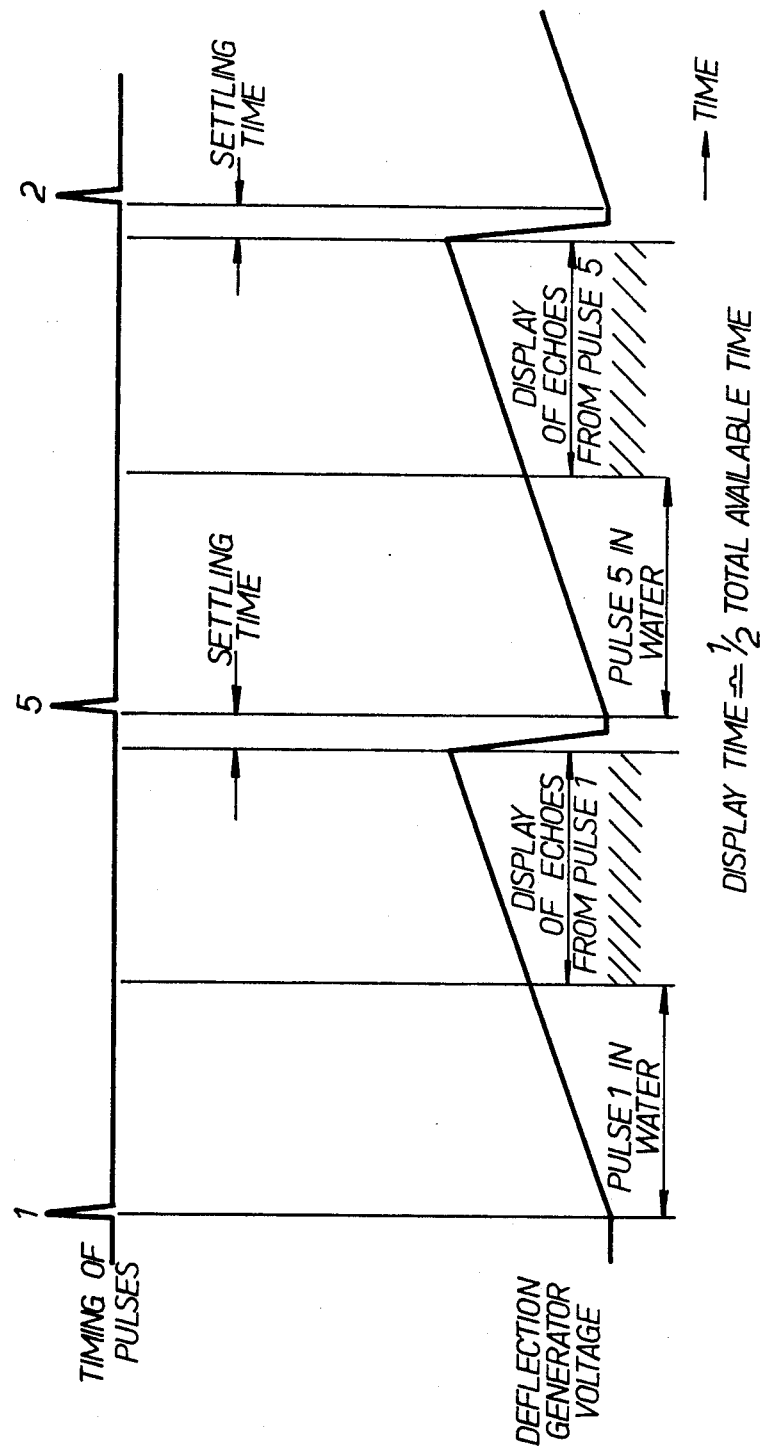
Figure 9:
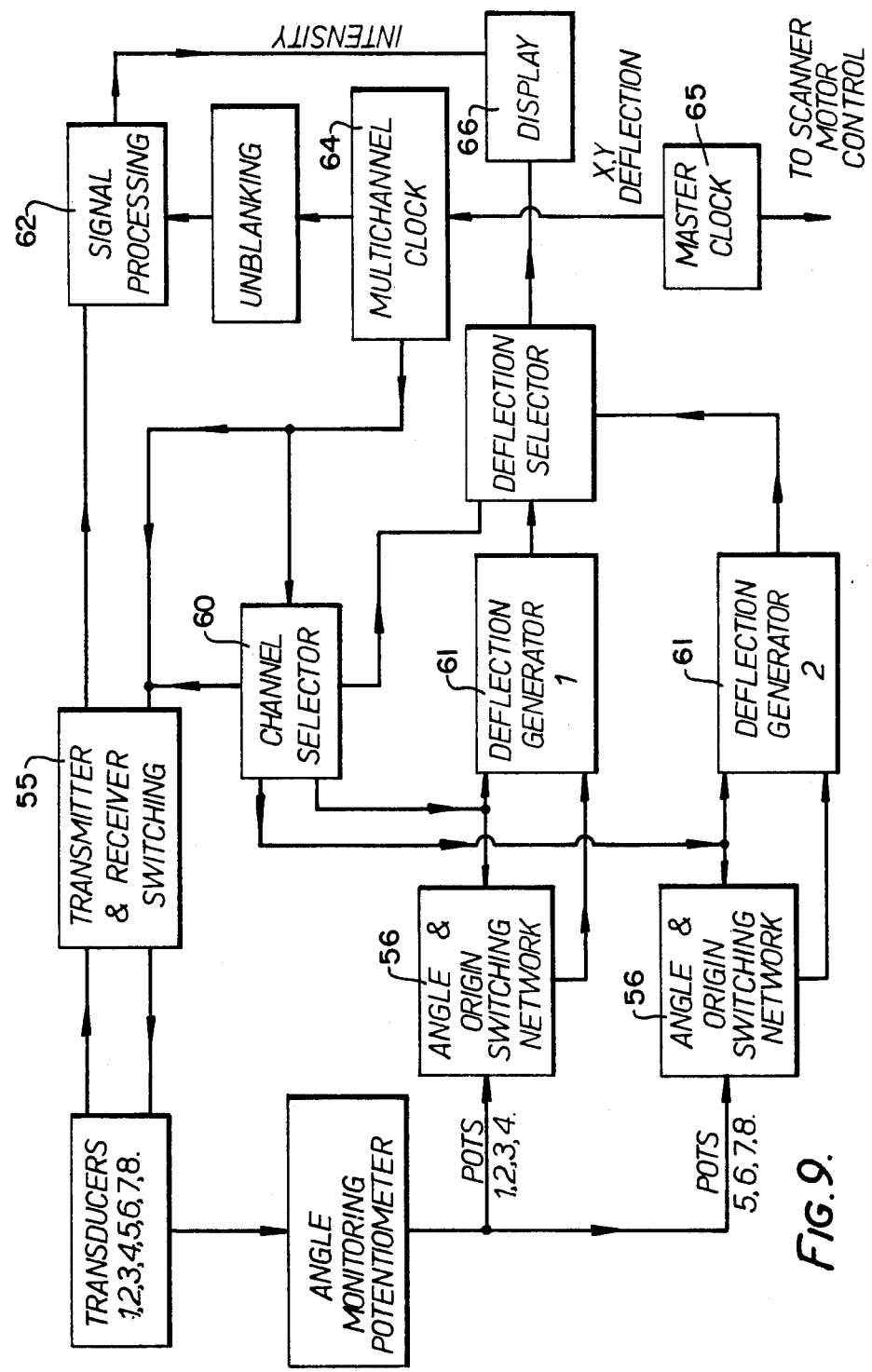

FIG. 8 graphically depicts a "scattered" mode of operation of the apparatus utilising the circuit of FIG. 5;

FIG. 9 shows a modification of the circuit of FIG. 5; and

Figure 10:
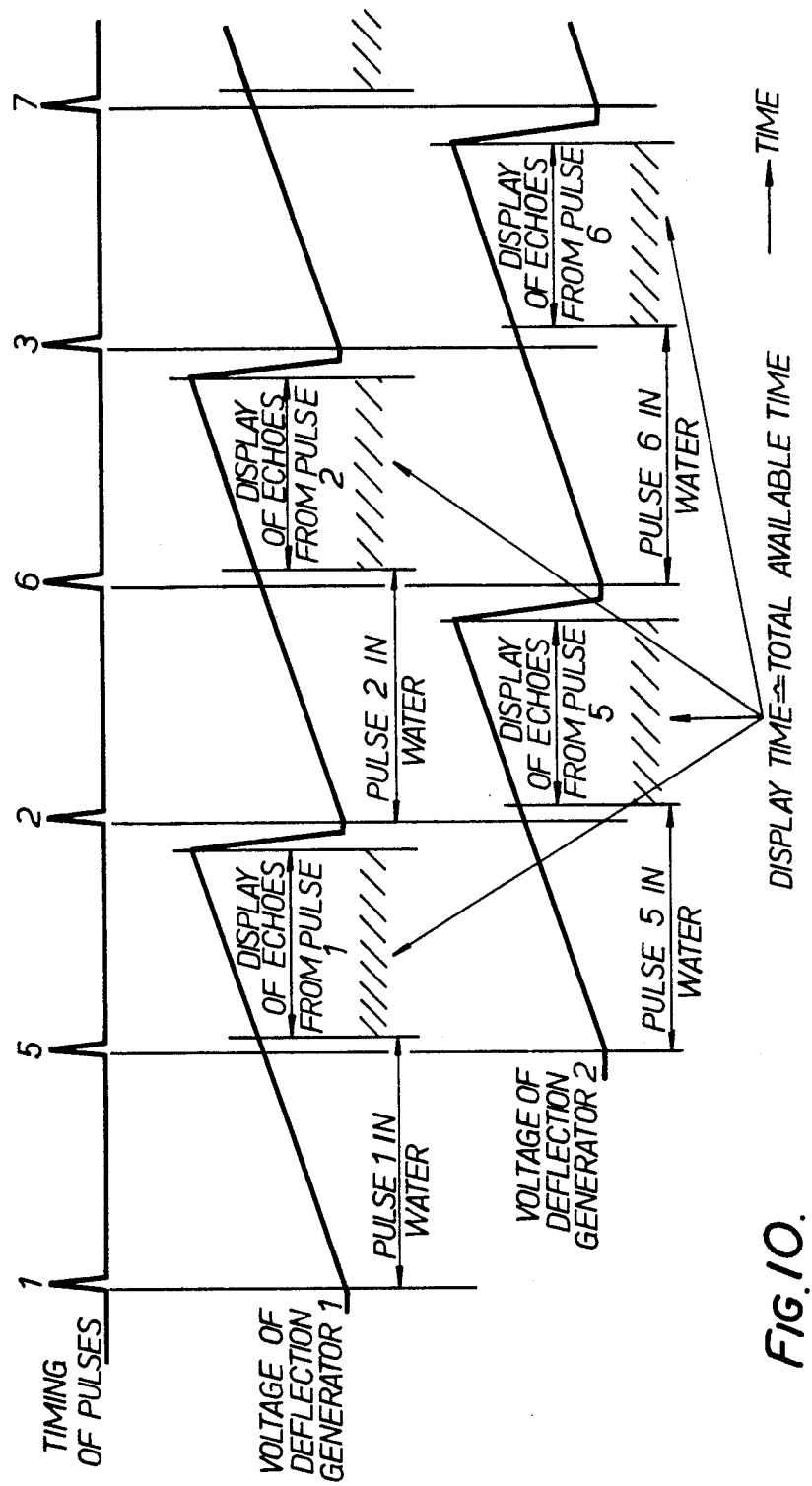

FIG. 10 graphically depicts an alternative mode of operation of the apparatus utilising the modified circuit of FIG. 9.

Figure 1:
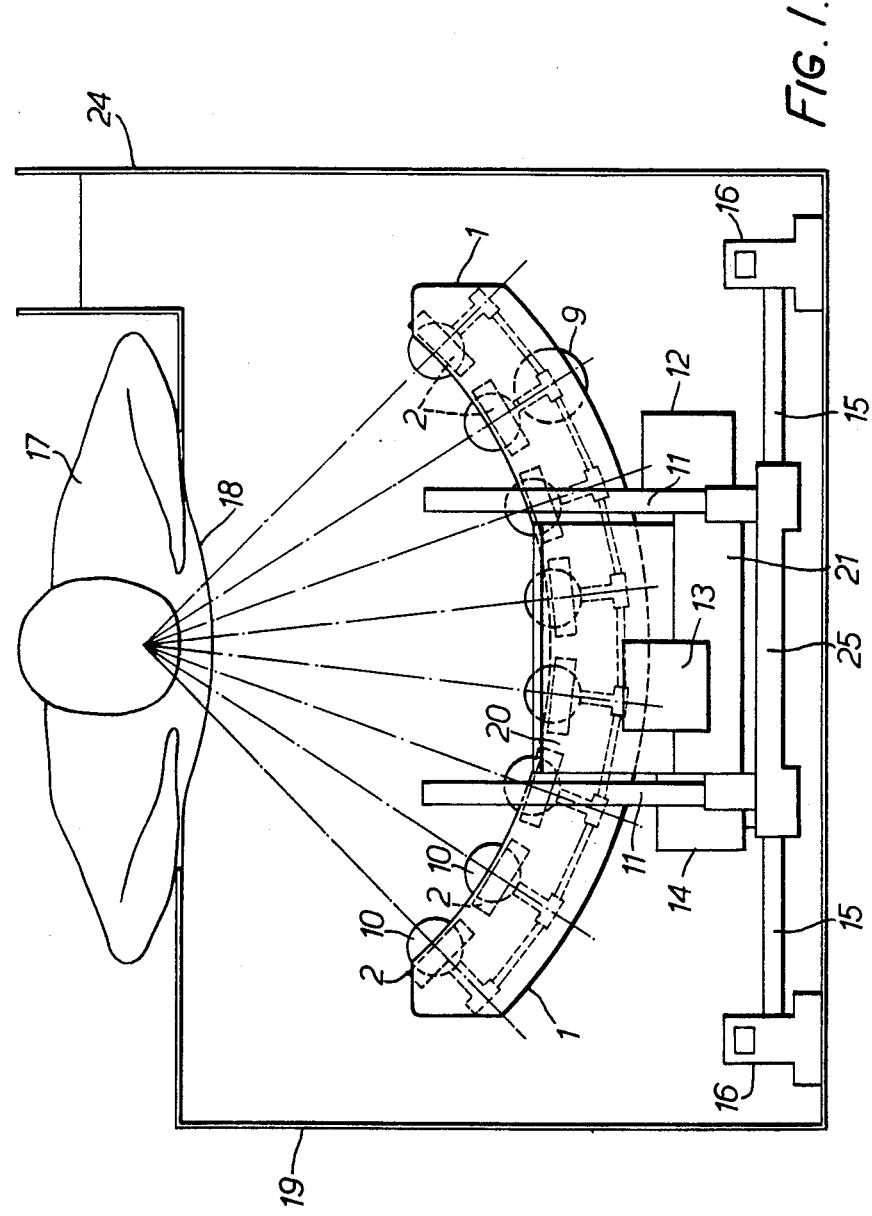
FIGS. 1 to 3 illustrate schematically apparatus in accordance with the present invention.
Figure 2:
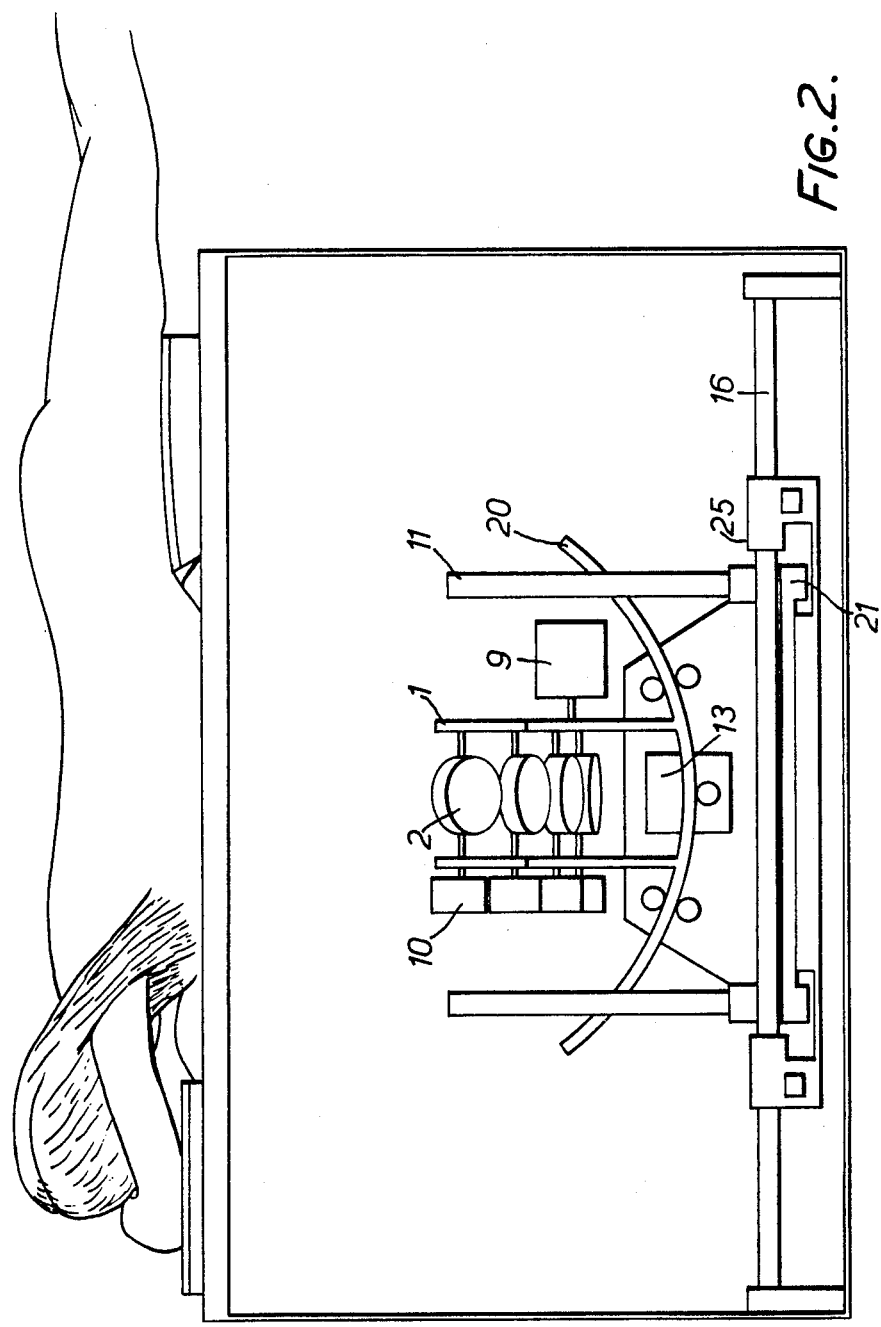
Figure 3:
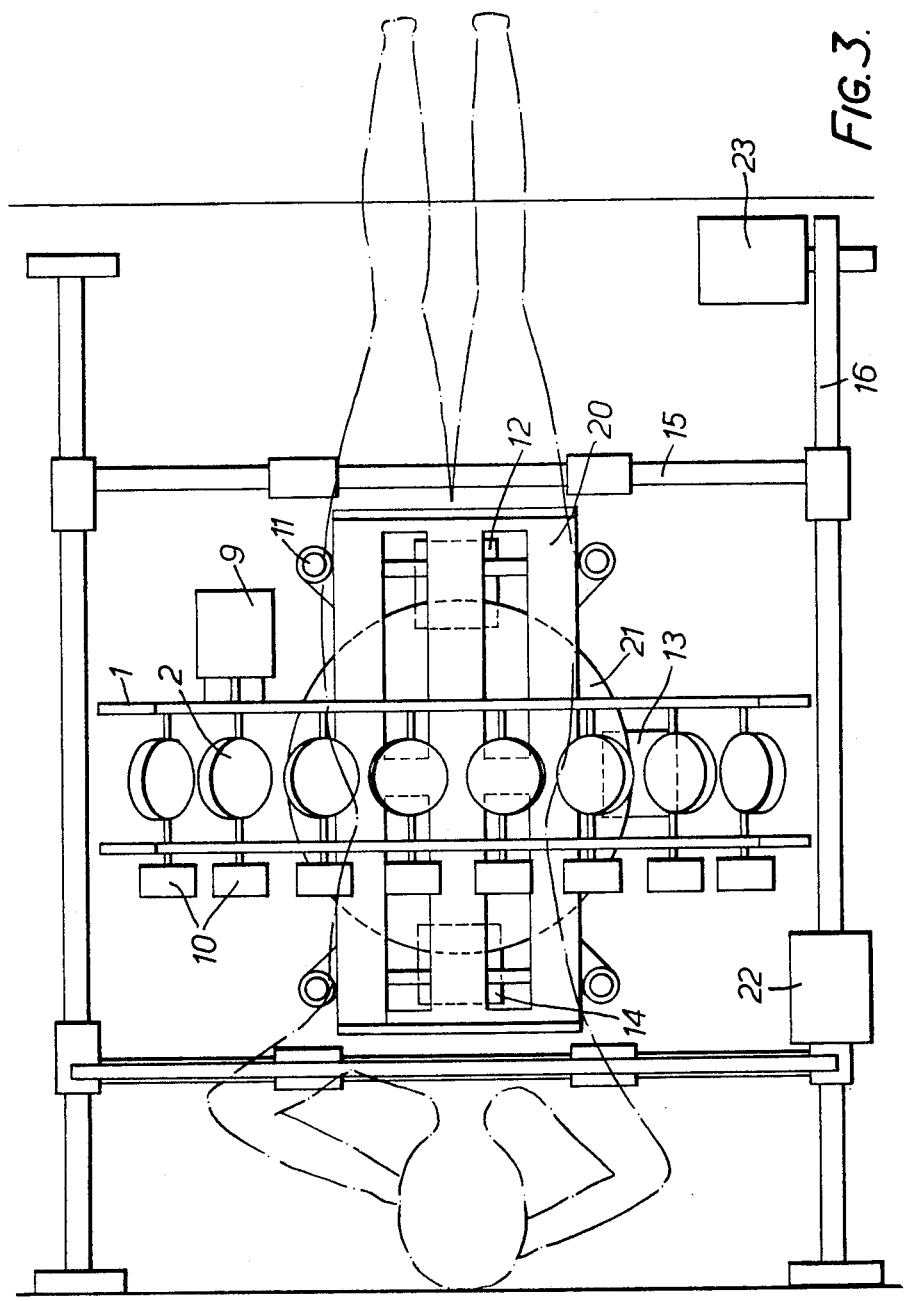

As shown in FIGS. 1 to 3 of the drawings, the apparatus of the present invention comprises a housing 19 in the form of a couch upon which a patient 17 can be positioned. The patient 17 is positioned with the region to be examined placed in contact with a flexible coupling membrane 18 which seals an aperture in the top of the housing. Housing 19 is filled with a coupling medium such as water and is provided with a header tank as at 24 to maintain proper contact between the patient and the membrane.

Figure 4:
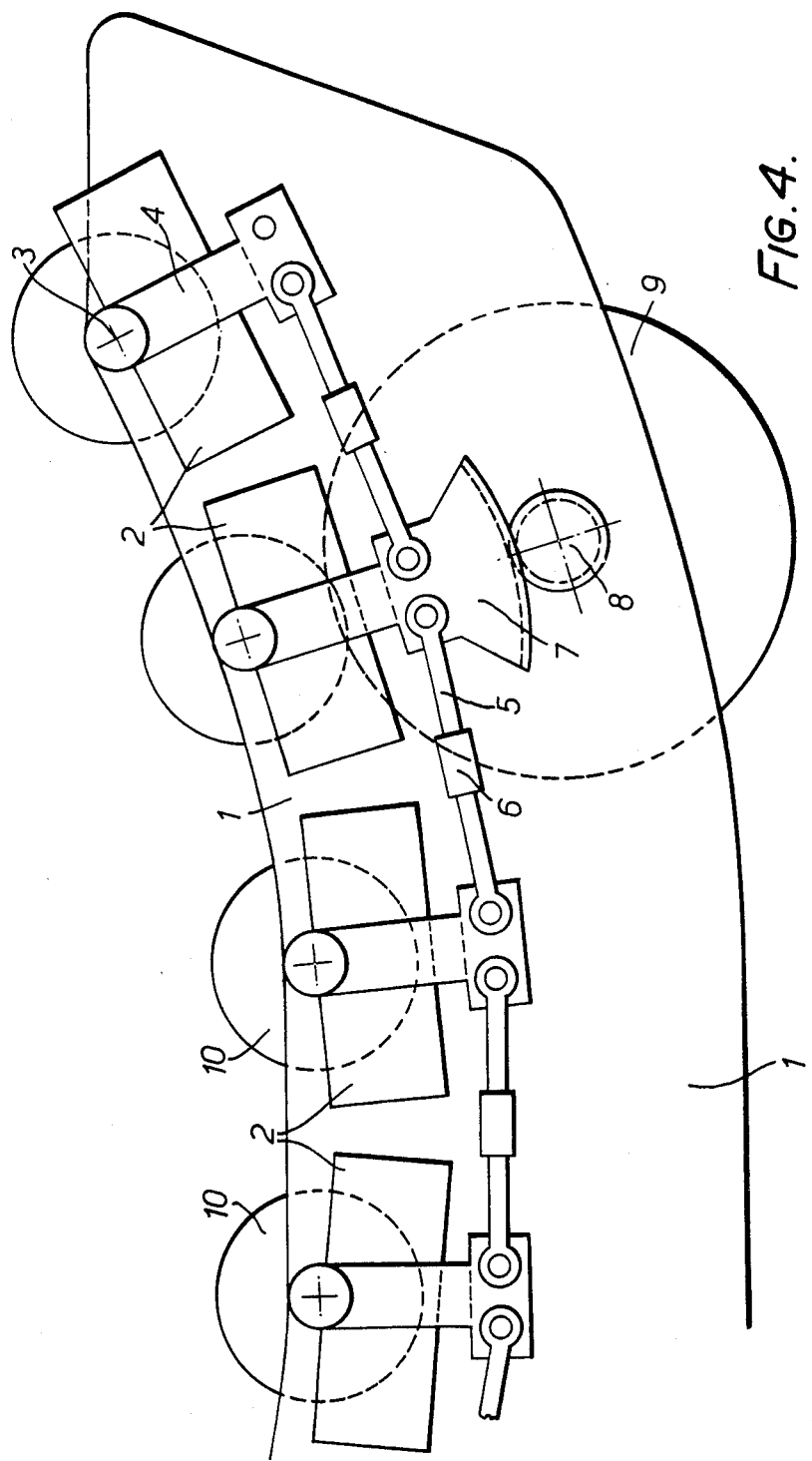
FIG. 4 illustrates in more detail the mechanism for oscillation of the transducers of the apparatus of FIGS. 1 to 3.

Located within the housing 19 and immersed in the coupling medium is a plurality of transducers 2 spatially mounted in a main supporting arm 1 so as to be capable of oscillating in the plane of the arm, thereby directing the respective pulses of ultrasonic energy along beams which are steerable in said plane. Eight transducers are shown in the FIGS. by way of example, however it will be appreciated that this number may be increased or decreased as desired. As shown in greater detail in FIG. 4, each transducer 2 is arranged to oscillate about pivot center 3 by action of oscillator arm 4. The respective oscillator arms 4 of each of the transducers 2 are coupled by links 5 which are provided with adjusters 6 to enable accurate positioning of the transducers 2 with respect to each other and the arm 1. One of the oscillator arms 4 is provided with a sector gear 7 which meshes with a geared output 8 of motor 9, attached to arm 1. It will be apparent that rotation of the shaft 8 of the motor 9 will result in simultaneous pivoting of each of the transducers 2 about its pivot center 3. The position or angle of each transducer is monitored by means of monitoring potentiometers 10.

Referring again to FIG. 1, main arm 1 is mounted on a main frame which is slidable towards and away from the patient 17 to enable positioning of the transducers mounted on arm 1 relative to the patient. The main frame is slidable on pillars 11 and movement along these pillars is controlled by motor 12, for example, by means of a rack and pinion drive. The main frame is also mounted on a carriage 25 which slides along a track 15 controlled by motor 22 (FIG. 3), again by means of a rack and pinion drive or the like. As depicted, the apparatus enables movement of carriage 25 along track 15 transverse to the patient 17 in the position depicted. Longitudinal movement of the arm 1 with respect to the patient is effected by movement along track 16 provided by motor 23 (FIG. 3) again, for example, by means of a rack and pinion drive.

As best seen in FIG. 2, arm 1 is mounted on a frame 20 which is supported by bearings or the like on carriage 25 for tilting motion with respect to the patient. Thus frame 20 is provided with an arcuate track section 20 which engages the shaft of motor 13, for example in a rack and pinion type drive, for tilting of the arm. Frame 20 is in turn mounted on turntable 21 which provides rotary motion of the arm 1 relative to the carriage 25, this rotary motion being controlled by motor 14. It will thus be apparent that by provision of appropriate mechanisms supporting arm 1, this arm can be positioned transversely, longitudinally, or toward or away from the patient. Further, the arm may be tilted or rotated relative to the patient to enable any desired plane of scan of the transducers 2. By way of example, the arm may be rotated in increments of 1° through 180° to give transverse, longitudinal or oblique echograms, and it may be tilted in increments of 1° through an angle of ±30° to give inclined section. The tilting movement of the arm is designed to pivot about the patients skin line minimising the translational movement of the scanning plane normally obtained with tilting. The arm may also be translated in the "x", "y" and "z" directions in increments ranging from 1 mm to 2 cm to give automatic acquisition of a number of parallel echograms separated by the selected distance. With the water coupling method all of these sections are obtained without changing the coupling to the patient thus allowing reliable cross correlation of detail in echograms obtained in different planes.

Preferably, all movement of the transducer means is powered by stepper motors. These have the advantage that their operation is controlled by the application of electrical pulses. For oscillatory motion of the transducers the rate of application is gradually built up, then kept constant during the echogram forming period and then gradually slowed down giving a reproducible even motion necessary for the attainment of a consistent grey scale and reducing the vibrations set up during acceleration of deceleration of the transducers. Stepper motors are also amenable to control by computers and all of the motions of the scanner may be placed under computer control.

The rapid rate of acquisition of high quality echograms has obvious advantages. It reduces blurring of detail caused by movement of structures during the echogram forming period and allows quasi real time viewing of the same section. Alternatively it allows the taking of many views from different angles making the examination somewhat similar to fluoroscopy. The total time necessary for the total examination is also significantly reduced allowing the same instrument to handle a must greater clinical load. The instrument also has the advantage that it utilises the minimum number of pulses to acquire a compound scan echogram and no tissue need be irradiated more than for example eight times. To minimise the irradiation dosage the attenuator settings of the echoscope control the level of the transmitted energy and not the gain of the receiver. The echoscope of this invention may also have the provision to switch off any set of transducers and also allow a simple scan to be obtained from any transducer.

The many degrees of movement of the apparatus of this invention makes it very versatile and it can be used in a variety of other modes of operation. For instance by combining a translational movement in the length direction of the arm, a compound scan echogram is obtained where the origin of oscillation of the transducers is moved. This mode of operation is useful in circumstances where it is desirable to view around some overlying shadowing structures such as ribs. This translation movement also reduces the Moires interference pattern obtained in the stationary mode of operation. The translation movement in this case need not be large, a movement corresponding to the inter transducer distance being adequate and this movement may be achieved in the same time as that taken for the single oscillatory movement.

In another mode of operation all of the transducers may be made to function as a single transducer corresponding to the size of the arm, and focusing techniques of the type used in annular phased array transducers may be used to generate a highly focused line of sight along the axis of the arm. A linear scan may then be formed by translating the arm in the length direction.

The multiple transducer configuration of the echoscope may be used to examine tissues in the single transmit-multi receiver mode of operation analogous to the multi-channel receiver operation used in seismology. Cross-correlation of information received by the multiple transducer may then be used to reduce multiple reflection artifacts in tissue and to measure local values of velocity in the various visualised tissues.

The echo scattering cross-section of tissue may also be obtained by two methods with the echoscope. In the first method, the tilting motion of the echoscope is used, the echo scattering cross-section being obtained from tissue at a depth corresponding to the projection from the transducer to the axis of rotation of the tilting motion. For a transducer facing vertically up this depth is equal to the radius of curvature of the tilting motion. Alternatively, by pointing the transducers to cross at the center, the echo scattering cross-section of tissue lying at the radius of curvature of the arm may be obtained by rotating the arm. The first method gives the echo scattering cross as a function of the angle in a fixed plane while the second method gives the value of this parameter when viewed at constant angle in a variable plane. In both methods the multiple transducer nature of the echoscope also allows a relatively coarse two dimensional dependence of the parameter.

Figure 6:
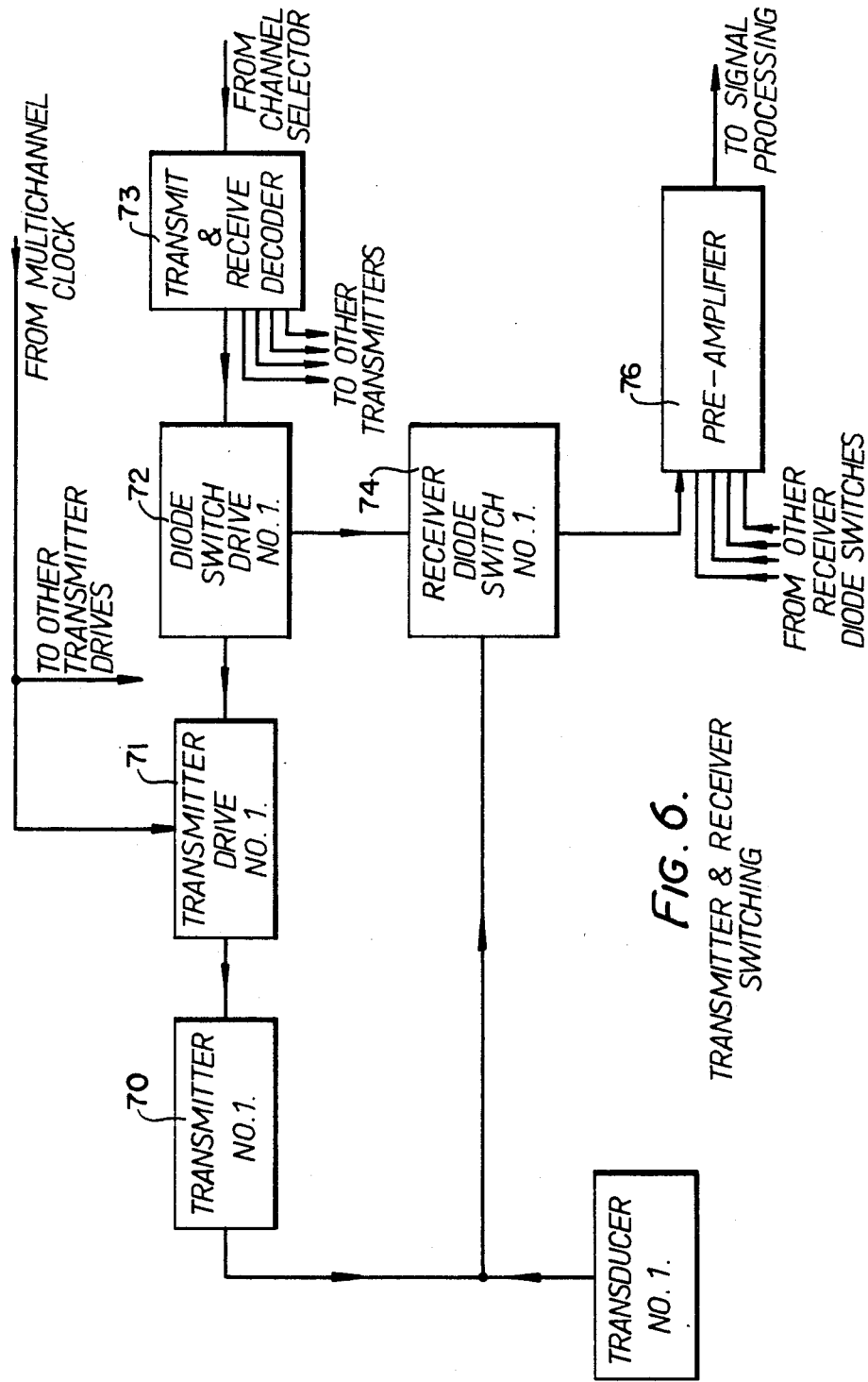
FIG. 6 shows a transmitter and receiver switching block diagram for the circuit of FIG. 5.
Figure 7:
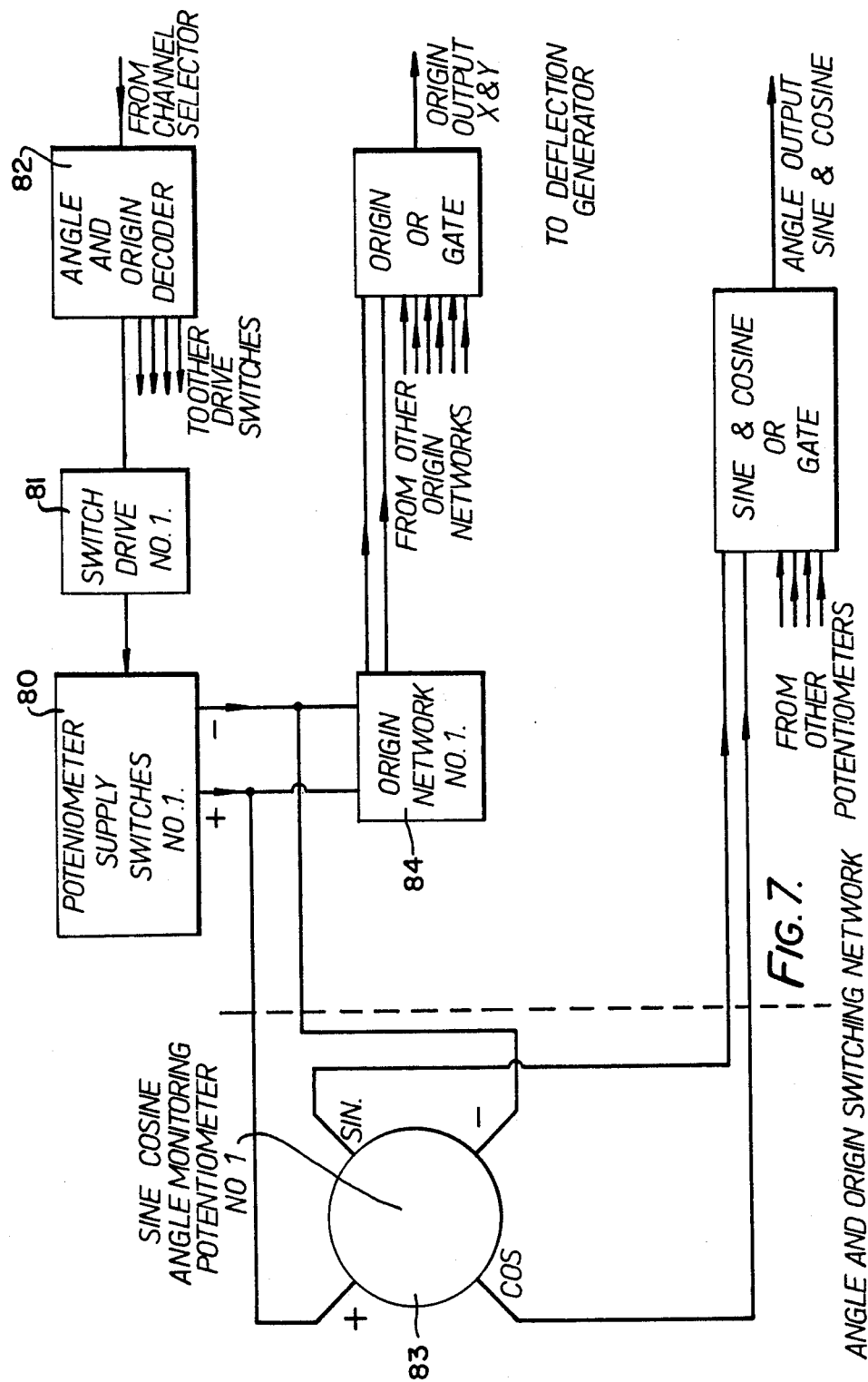
FIG. 7 shows a block diagram of an angle and origin switching network for the circuit of FIG. 5.

One mode of operation of the apparatus in accordance with this invention is depicted in FIGS. 5 to 7.

As shown in FIG. 5, the master clock 65 provides basic time impulses to initiate multi-channel clock 64 and to drive motors 52, 54 via the motor controller 57, 58, 59.

The multi-channel clock 64 outputs, in turn, trigger pulses to each channel upon receiving a pulse from the master clock 65.

The channel selector 60 counts trigger pulses and sends a binary channel address code to transmitter and receiver switching network 55 and to angle and origin switching network 56.

The signal processor 62 processes echoes from transmitter and receiver switching network 55, which echo signals are fed together with blanking pulses to the intensity modulation input of the display unit 66.

Deflection generator 61 generates X and Y deflection voltages from signals received from angle and origin switching network 56.

FIG. 6 shows the transmitter and receiver switching network in greater detail. As seen in FIG. 6, transmit and receive decoder 73 decodes channel selector output signals from channel selector 60 to activate the correct diode switch drive 72 and transmitter drive 71. The multi-channel clock output then triggers the transmitter drive 71 to energize the transmitter 70.

Receiver diode switch 74 is energized by the decoder 73 via diode switch drive 72 which allows echo signals to pass to the preamplifier 76.

In FIG. 7, the angle and origin switching network 56 of FIG. 5 is more fully disclosed. As seen in FIG. 7, angle and origin decoder 82 decodes the channel selector output to activate the correct switch drive 81 and hence turn on the correct potentiometer supply switch 80. The supply switch 80 supplies reference voltages to the sine cosine angle monitoring potentiometer 83 and to the origin network 84.

The X and Y origin coordinates from the origin network 84 and the sine and cosine angle output from the potentiometer 83 are fed via their respective OR gates to the deflection generators 61 (see FIG. 5) within the processing electronics.

FIG. 8 illustrates graphically the "scattered" mode of operation which can be adopted using the circuits of FIGS. 5 to 7. It will be apparent from FIG. 8 that by timing the pulses such that pulse 1 is followed by pulse 5, rather than directly by pulse 2, pulse 5 may be transmitted through the water acting as the coupling medium after a brief lapse of time, the settling time, following completion of the display of echoes from pulse 1. As described above, in this "scattered" mode of operation, transmission of pulse 5 through the coupling medium need not be delayed until multiple reflections from pulse 1 die down as the beam of pulse 5 is substantially spaced from the beam of pulse 1. Of course, when pulse 2 is transmitted after the display of echoes from pulse 5 and a brief settling time the multiple reflections from pulse 1 will by then have died down. FIG. 8 illustrates that by use of this mode of operation a display time approximating half the total available time can be achieved.

FIG. 9 shows a modification of the circuit of FIG. 5 in which deflection generator 61 thereof is replaced by deflection generator 1, deflection generator 2 and a deflection selector. Separate angle and origin switching networks are also provided for each deflection generator. Other integers of FIG. 9 which are not shown are as shown in FIG. 5.

FIG. 10 illustrates an alternative mode of operation of the apparatus of the present invention, utilising the modified circuit of FIG. 9. In this alternative mode of operation, the existence of a second deflection generator enables pulse 5 to be transmitted through the coupling medium at substantially the same time as the display of echoes from pulse 1 is effected using the first deflection generator. Thus, display of echoes from pulse 5 can be effected almost immediately after completion of display of echoes from pulse 1. At substantially the same time, pulse 2 can be transmitted through the coupling medium utilising the first deflection generator. FIG. 10 illustrates that by use of this mode of operation a display time approximating the total available time can be achieved.

From the foregoing description it will therefore be appreciated that the present invention enables more rapid and complete scanning of an object subject to ultrasonic examination. While the invention has been described with reference to illustrative embodiments, it will be generally understood by those skilled in the art that various changes may be made and equivalents be substituted for elements thereof without departing from the true spirit and scope of the invention.

The claims defining the invention are as follows:

1. Apparatus for use in the ultrasonic examination of an object, said apparatus comprising:
    a housing adapted to be filled with a liquid coupling medium, said housing having a substantially horizontal upper surface and being provided with an aperture in said surface;
    a flexible coupling membrane covering said aperture in a liquidtight seal;
    transducer means contained within said housing and adapted to be immersed in said coupling medium, said transducer means comprising means for transmitting pulses of ultrasonic energy through said aperture into an object positioned adjacent said aperture and means for receiving echoes of said pulses of ultrasonic energy reflected through said aperture by acoustic impedance discontinuities within the object; and
    an open storage header tank for said liquid coupling medium in communication with said housing and the atmosphere to maintain the pressure of said coupling membrane constant during flexing of the membrane.

2. Apparatus as defined in claim 1 wherein said transducer means comprises a plurality of transducers mounted in an arm, said arm being mounted within the housing by a supporting mechanism for movement thereof with respect to the object.

3. Apparatus as defined in claim 2, wherein said arm is curved about a point spaced a predetermined distance above said membrane.

4. Apparatus as defined in claim 2, wherein said supporting mechanism includes means to move said arm towards and away from said object, means to move said arm longitudinally and transversely with respect to an axis of said object, and means to rotate and tilt said arm with respect to said object.

5. Apparatus as defined in claim 2 wherein each transducer of said plurality of transducers is mounted in said arm for pivotal movement in the plane of the arm, and said transducers are mechanically linked for simultaneous movement.

* * * * *